United States Patent [19]

Humes

[11] Patent Number: 5,429,938
[45] Date of Patent: Jul. 4, 1995

[54] METHODS AND COMPOSITIONS FOR ISOLATION AND GROWTH OF KIDNEY TUBULE STEM CELLS, IN VITRO KIDNEY TUBULOGENESIS AND EX VIVO CONSTRUCTION OF RENAL TUBULES

[75] Inventor: H. David Humes, Ann Arbor, Mich.

[73] Assignee: University of Michigan, Ann Arbor, Mich.

[21] Appl. No.: 844,758

[22] Filed: Mar. 2, 1992

[51] Int. Cl.⁶ .............................................. A61K 38/18
[52] U.S. Cl. ................................ 435/240.2; 530/350; 530/399; 514/2
[58] Field of Search ............. 435/240.1, 240.2, 240.21; 514/2; 530/399, 350

[56] References Cited

PUBLICATIONS

Vasios, *Proc. Natl Acad Sci* 86 9099–9103 (1989).
Taub, *Proc Natl Acad Sci* 87 4002–4006, 1990.
Humes *Laboratory Investigation* 64, 538–545 1991.
Montesano *Cell* 67, 901–908, 1991.

*Primary Examiner*—Jill Warden
*Assistant Examiner*—David Lukton
*Attorney, Agent, or Firm*—Oblon, Spivak, McClelland, Maier, & Neustadt

[57] ABSTRACT

Methods, including culture media conditions, which provide for isolation and purification of renal tubule stem cells and for in vitro kidney tubulogenesis are disclosed. The methods rely on culturing adult kidney cells in a culture media treated with combinations of transforming growth factor-$\beta_1$, epidermal growth factor, and all-trans retinoic acid.

16 Claims, No Drawings

METHODS AND COMPOSITIONS FOR ISOLATION AND GROWTH OF KIDNEY TUBULE STEM CELLS, IN VITRO KIDNEY TUBULOGENESIS AND EX VIVO CONSTRUCTION OF RENAL TUBULES

BACKGROUND OF THE INVENTION

1. Field of the Invention

This invention relates to methods and compositions for isolating, growing and transforming kidney tubule stem cells.

2. Discussion of the Background

Renal failure is a common clinical syndrome, defined as a decline in renal function, either acutely or chronically. The clinical manifestations of this disorder arise from a decline in glomerular filtration rate and an inability of the kidney to excrete the toxic metabolic wastes produced by the body. The complete treatment of this condition is dependent upon the replacement of filtrative, reabsorptive, homeostatic and endocrine functions of the kidney as an integrated organ structure.

In this regard, the function of a tissue is critically dependent upon the spatial arrangement of its constituent cells. The precise molecular determinants of such pattern formation both in vitro and in vivo is complicated, but soluble factors, such as growth factors, and insoluble factors, such as extracellular matrix molecules, most likely play fundamental roles in this process. Soluble molecules include both growth promoters (epidermal growth factor) and growth inhibitors (transforming growth factor-$\beta$). Insoluble factors include complex extracellular matrices (collagen gels, Matrigel) or extracellular matrix (ECM) molecules (laminin, fibronectin, collagen types I and IV).

This critical interplay of structure and function is demonstrated in the embryonic morphogenesis of the kidney, which is dependent upon a finely orchestrated interaction between mesenchyme and epithelium. The initial steps in differentiated nephrogenesis are followed by the development of tubule epithelial cell polarity and lumen formation. Coincident with the onset of cell polarity and tubulogenesis, as defined by both morphologic and directional transport properties, is the appearance of the A chain of laminin, a cell attachment protein of the basement membrane, in the basal regions of the mesenchymal cell aggregate. A sequential series of growth and further differentiation processes then follows to result eventually in a fully formed and functional kidney.

If this complex process of kidney organogenesis could be mimicked in vitro, novel methods for the treatment of renal failure could become available. Various tissue engineering products could be constructed from both semi-synthetic and organic components for complete replacement of renal function in patients with renal failure. Such advances might also allow the development of bioreactors comprising purely organic material for the substitution of renal function in a patient whose kidneys are compromised. These developments could also allow for kidney organogenesis, resulting in the growth of an organic kidney in vitro, from the isolation of renal tubule stem cells from a donor and subsequent growth and differentiation. The in vitro kidney could later be transplanted to the donor of the original renal cells, resulting in replacement of renal function without any fear of transplant rejection or immunosuppressive therapy. The availability of renal tubule stem cells could also promote an efficient process for incorporation of various genes into renal cells for gene therapy of various diseases.

However, such developments are predicated upon the development of a culture system which allows for isolation and growth of kidney tubule stem cells and for in vitro tubulogenesis.

Such a culture system has not been achieved in the prior art, although in vivo kidney cells have demonstrated a potential for differentiation and regeneration. As demonstrated by Humes et al., *J. Clin. Invest.* 84:1757–61 (1989) and by Coimbra et al., *Am. J. Physiol.* 259:F438–F443 (1990), complete recovery of renal function can occur after severe nephrotoxic or ischemic acute renal injury that was of a magnitude to produce complete renal failure. Thus, some subset of renal proximal tubule cells apparently has the ability in vivo to regenerate and form a fully functional, differentiated epithelium. However, such results are doubtlessly the result of the complex interaction of a large number of biological factors responsible for growth, differentiation, pattern formation and morphogenesis of the renal tubule.

Certain of these factors have been identified and employed in renal cell cultures. TGF-$\beta_1$ has been recently shown to transform a monolayer of renal proximal tubule cells in primary culture into a three-dimensional adhesive aggregate of cells, see Humes et al, *Lab. Invest.* 64:538–545 (1991). EGF has been shown to be a potent growth promoter for renal epithelial cells, see Norman et al, *Am. J. Physiol.* 253:F299–F 309 (1987). Retinoic acid has been reported to increase laminin synthesis in embryonic cell lines by promoting laminin gene transcription, see Dziad et al, *Devel. Biol.* 111:372–382 (1985); Vasios et al, *Proc. Natl. Acad. Sci. (USA)* 86:9099–9103 (1989); and Rogers et al, *J. Cell. Biol.* 110:1767–1777 (1990). However, these efforts of the prior art have all failed to evoke tubulogenesis in renal cell cultures. Such tubulogenesis is the first step towards in vitro kidney organogenesis.

SUMMARY OF THE INVENTION

Accordingly, it is an object of this invention to provide novel methods, including culture media conditions, for in vitro kidney tubulogenesis.

It is another object of the present invention to provide novel methods for isolating and growing kidney tubule stem cells.

It is another object of this invention to provide a novel, functioning ex vivo kidney tubule tissue system.

It is another object of this invention to provide novel methods, including culture media conditions, for culturing renal tubule stem cells so as to effect gene therapy upon said cells.

The present invention provides methods and composition which satisfy all of the above objects of this invention, and other objects, as will be apparent from the description of the invention given hereinbelow.

The present invention is based on the inventor's discovery of novel methods, including culture media conditions, which provide for isolation and growth of kidney tubule stem cells, for in vitro kidney tubulogenesis and for ex vivo construction of renal tubules. These methods rely on culturing renal proximal tubule cells in a hormonally-defined culture medium which is treated with combinations of transforming growth factor-$\beta_1$ (TGF-$\beta_1$), epidermal growth factor (EGF) and the retinoid, all-trans retinoic acid (RA), while maintaining the culture under physiologically acceptable conditions.

The inventor has discovered that the administration of TGF-βhd 1, EGF and all-trans retinoic acid transform a confluent monolayer of renal proximal tubule cells into three-dimensional cell aggregates containing lumens within the interior of the cell clusters. The lumens were bordered by tubule cells possessing a polarized epithelial cell phenotype with extensive microvilli formation and tight junctional complexes along the luminal border.

In one embodiment all three factors are used to isolate and grow kidney tubule stem cells and to induce this phenotypic transformation. In an alternate embodiment all-trans retinoic acid and EGF are employed to isolate and grow kidney tubule stem cells and to induce tubulogenesis. It is possible to substitute transforming growth factor-α for EGF. These results demonstrate that the growth factors, TGF-$β_1$ and EGF, and the retinoid, all-trans retinoic acid, promote tubulogenesis of adult renal proximal tubule cells in kidney cell culture.

DETAILED DESCRIPTION OF THE PREFERRED EMBODIMENTS

The inventor has found that the treatment of a hormonally-defined renal cell culture with transforming growth factor-$β_1$, epidermal growth factor, and all-trans retinoic acid transformed a confluent monolayer of renal proximal tubule cells into epithelial cell aggregates containing lumens, bordered by cells with a differentiated polarized epithelial cell phenotype.

In a preferred embodiment of the present invention, transforming growth factor-$β_1$ is administered so as to achieve a concentration of from 0.1 ng/ml–1 mg/ml, epidermal growth factor in a concentration range of from 0.1 nM to 1 μM, and all-trans retinoic acid in a concentration range of from 0.01 μM to 100 μM.

Another, optional but important, embodiment of the present invention, resides in the addition of soluble factors to the renal tubule stem cell culture. In a particularly preferred aspect of this embodiment, these soluble factors include fetal calf serum, prostagladins, hydrocortisone trioodothyronine, selenium, fibroblastic growth factor, transforming growth factor-α, hepatocyte growth factor, and combinations thereof.

These soluble factors are preferably added in the following concentrations: fetal calf serum, 3–25% (volume/volume) of growth media; prostaglandin $E_1$, 1 to 100 ng/ml; triiodothyronine, 0.1 nM to 1 μM; selenium, 0.001 to 1.00 μM; cholesterol, 1.0 nM to 0.10 μM; transferrin, 1 to 50 μg/ml; transforming growth factor-α, 0.1 nM to 1 μM; insulin, 1–50 μg/ml; hydrocortisone, 1 nm to 1 μM; and hepatocyte growth factor 0.1 ng/ml to 100 ng/ml.

Another, optional but important, embodiment of the present invention, resides in the addition of insoluble factors to the renal tubular stem cell culture. These insoluble factors include a variety of extracellular matrix molecules. Included in these extracellular matrix molecules are Type I collagen, Type IV collagen, laminin, proteoglycans, fibronectin, and combinations thereof.

These insoluble factors are preferably added in the following concentrations: collagen, Type I, 1 to 5 mg/ml; collagen, Type IV, 0.01 to 5 mg/ml; laminin, 10 to 1000 μg/ml; heparin sulfate, 10 to 1000 μg/ml; and heparin, 10 to 1000 μg/ml.

An additional preferred embodiment of the present invention resides in the addition of both soluble factors and insoluble factors to the renal tubule stem cell cultures.

In the present invention, the techniques used to obtain, collect and grow the renal cells and the culture systems in which the renal cells are grown are conventional ones and are described in Taub et al, *J. Biol. Chem.*, 254, 11440–11444; Taub et al, *J. Cell Physiol.*, 106 191–199; Taub et al, *J. Supramol. Struct*, 11, 207–216; Taub et al, *J. Cell Physiol*, 105, 369–378; Taub et al, *Proc. Nat. Accad. Sci. USA*, 76, 3338–3342; Taub et al, *Ann. New York Acad Sci.*, 372, 406–421; Taub et al, *J. Supramol. Struct.*, 15, 63–72; and Taub et al, *J. Cell Physiol*, 114, 153–161; which are incorporated herein by reference.

In the present specification, the terms treatment and treating refer to a process or means of exposing the cultured cells to the substance being administered. The specific method of treatment varies, depending on the properties of the substance, If added in aliquots, the flow of the aliquot being added may be by gravity, by pump, or by any other suitable means. The flow may be in any direction or multiplicity of directions, depending upon the configuration and packing of the culture. Preferably, the substance is added in a manner such that it contacts the cell mass. Most preferably, it is added to the culture in a manner mimicking in vivo perfusion, i.e., it is perfused through at least part of the cell mass and up to the whole cell mass.

The term tubulogenesis denotes the de novo construction of three dimensional cell aggregates containing lumens within the interior of the cell clusters. Such lumens are bordered by tubule cells possessing a polarized epithelial cell phenotype with extensive microvilli formation and tight junctional complexes along the laminal border.

In one embodiment, the ex vivo renal tubule tissue system may be implanted in a patient in need thereof. The renal cells comprising such a tubule tissue system may be either transformed or non-transformed cells. The implantation may be achieved by conventional techniques, such as, by graft or insertion.

Moreover, the renal tubule stem cell cultures of the present invention may serve as an important target in gene therapy. Gene therapy is a rapidly growing field in medicine which is of inestimable clinical potential. It comprises the insertion of genes into cells for the purpose of medicinal therapy. Research in gene therapy has been on-going for several years and has been conducted in several types of cells in vitro and in animal studies, and has recently entered the first human clinical trial. Gene therapy has many potential uses in treating disease and has been reviewed extensively. See, e.g., Boggs, *Int. J. Cell Cloning* 8, 80 (1990), Kohn et al, *Cancer Invest.* 7, 179 (1989), Lehn, *Bone Marrow Transp.* 5, 287 (1990), and Verma, *Scientific Amer.* 68 (1990). Suitable genetic diseases and disorders that may be treated with the transformed renal tubule stem cells of the present invention are described in Ellis, *Inborn Errors of Metabolism*, Croom Helm London, 1980, and Galjaard, *Genetic Metabolic Diseases*, Elsevier, N.Y., 1980, which are incorporated herein by reference.

The renal tubule stem cell system is an ideal choice for gene therapy. However, up to the present time renal tubule stem cells have not been accessible. With the methods and compositions of the present invention, renal tubule stem cells are now readily available for gene therapy, can be maintained in culture for unlimited periods of time, and upon reimplantation, may replace kidney function.

The renal tubule stem cells can be transformed with one or more genes providing for desired traits. Methods for transforming mammalian cells are well known and there is an extensive literature of which only a few references have been previously given. The constructs may employ the naturally occurring transcriptional initiation regulatory region, comprising the promoter and, as appropriate the enhancer, or a different transcriptional initiation region may be involved, which may be inducible or constitutive.

A large number of transcriptional initiation regions are available which are inducible or constitutive, may be associated with a naturally occurring enhancer, or an enhancer may be provided, may be induced only in a particular cell type, or may be functional in a plurality or all cell types. The transcriptional initiation region may be derived from a virus, a naturally occurring gene, may be synthesized, or combinations thereof.

Promoters which are available and have found use include the chromosomal promoters, such as the mouse or human metallothionein-I or II promoters, actin promoter, etc., or viral promoters, such as SV40 early gene promoters, CMV promoter, adenovirus promoters, promoters associated with LTRs of retroviruses, etc. These promoters are available and may be readily inserted into appropriate vectors which comprise polylinkers for insertion of the transcriptional initiation region as well as the gene of interest. In other instances, expression vectors are available which provide for a polylinker between a transcriptional region, also providing for the various signals associated with the processing of the messenger for translation, i.e., the cap site and the polyadenylation signal. The construction of the expression cassette comprising the regulatory regions and the structural gene may employ one or more of restriction enzymes, adapters, polylinkers, in vitro mutagenesis, primer repair, resection, or the like.

The expression cassette will usually be part of a vector which will include a marker and one or more replication systems. The marker will allow for detection and/or selection of cells into which the expression cassette and marker have been introduced. Various markers may be employed, particularly markers which provide for resistance to a toxin, particularly an antibiotic. Preferably, gentamicin resistance is employed, which provides resistance to G418 for a mammalian cell host. The replication systems may comprise a prokaryotic replication system, which will allow for cloning during the various stages of bringing together the individual components of the expression cassette. The other replication system may be used for maintenance of an episomal element in the host cell, although for the most part the replication system will be selected so as to allow for integration of the expression cassette into a chromosome of the host.

The introduction of the expression cassette into the host may employ any of the commonly employed techniques, including transformation with calcium precipitated DNA, transfection, infection, electroporation, ballistic particles, or the like. Once the host cells have been transformed, they may be amplified in an appropriate nutrient medium having a selective agent, to select for those cells which comprise the marker. Surviving cells may then be amplified and used.

Host cells which may be employed include African green monkey cell line CV1, mouse cells NIH-3T3, normal human bone marrow fibroblasts, human spleen fibroblasts, normal mouse bone marrow fibroblasts, and normal mouse spleen fibroblasts. It should be noted that in some instances, depending upon the choice of vector and cell line, the cells may become neoplastic.

Once the vector for expressing the appropriate trait has been constructed, it may be used to transform the cells by any convenient means. The cells will be allowed to grow for sufficient time to ensure that the cells are viable and are capable of producing the desired traits.

The term transforming vector or cell transformation vector as used in the present invention refers to a DNA molecule, usually a small plasmid or bacteriophage DNA capable of self-replication in a host organism, and used to introduce a fragment of foreign DNA into a host celll.

Other features of the present invention will become apparent in the course of the following descriptions of exemplary embodiments which are given for illustration of the invention and are not intended to be limiting thereof.

EXEMPLARY EMBODIMENTS

Cell Culture

Rabbit renal proximal tubule cells were grown in primary culture by techniques reported by Humes et al. in Lab. Invest. 64:538-45 (1991). The cells were grown in 35 mm Corning culture dishes with serum-free, hormonally defined Dulbecco's Modified Eagle Hams F-12 media (1:1, v/v) containing L-glutamine, penicillin, streptomycin, 50 nM hydrocortisone, 5 µg/ml of insulin, and 5 µg/ml of transferrin. The cultures were maintained in a humidified 5% $CO_2$/95% air incubator at 37° C. Medium was changed every 3 to 5 days, depending on nutrient requirements based upon cell number. Cultures became confluent in 9 to 12 days. Once confluent, various agents as described below were added in 20 µl aliquots at various times to promote changes in morphologic phenotype or pattern formation.

Morphology

Specimens for ultrastructural analysis were fixed with 2% glutaraldehyde in Sorenson's buffer (pH 7.2, 310 mOsm). Postfixation occurred in 1% $OsO_4$ followed by dehydration in ethanol. Specimens were transferred through propylene oxide into monomer mixture (poly/Bed 812A, Araldite, DDSA and DMP-30) and polymerized at 60° C. Thin sections were stained with uranyl acetate and lead citrate, and examined in a Zeiss 9-S2 transmission electron microscope.

Materials

All reagents used were of the highest grade commercially available. All organic reagents were obtained from Sigma Chemical Company (St. Louis, Mo.) unless otherwise indicated. EGF (recombinant human) was obtained from Amgen Biologicals (Thousand Oaks, Calif.), TGF-$\beta_1$ (porcine platelets) from R & D Systems (Minneapolis, Minn.). TGF-$\beta_1$ was dissolved in 4 mm HCl and 1 mg/ml bovine serum albumin; EGF in aqueous buffer, and RA in 95% ethanol.

Results

Simultaneous treatment of density-arrested, confluent monolayers of adult rabbit renal proximal tubule cells with TGF-$\beta_1$, EGF, and RA resulted in a dramatic phenotypic transformation characterized by condensed aggregates of cells in cord-like structures. Evaluation of these cellular aggregates by light and transmission electron microscopy revealed the presence of lumen formation within the interior of the cell aggregates. The lumens were bordered by tubule cells possessing a polarized epithelial phenotype with extensive microvilli formation and tight junctional complexes along the lumenal border. Of note, in each aggregation of cells one or two lumen structures were usually observed in random sectioning of tissue culture preparations. The lumens and bordering polarized epithelial cells were surrounded by nonpolarized, adherent cells which did not possess tight junctional complexes.

All three factors are necessary for tubulogenesis, as demonstrated by the following experiments.

EXAMPLE 1

A density-arrested, confluent monolayer of renal proximal tubule cells in standard tissue culture was simultaneously treated with TGF-$\beta_1$ (10 ng/ml), EGF (1 nM), RA (0.1 $\mu$M). After 144 hours of treatment, the cell culture had undergone a transformation of the monolayer into adherent cell aggregates containing an area with a well defined lumen, as seen by light microscopy (magnification $\times 400$). Utilizing transmission microscopy, the lumen could be seen to be bordered by tubule cells possessing a polarized epithelial cell phenotype with well-developed epithelial microvilli (magnification $\times 6500$). Further magnification ($\times 19900$) with electron microscopy demonstrated that tight junctional complexes existed between the cells bordering the lumen near the apical surface.

COMPARATIVE EXAMPLE 2

Addition of TGF-$\beta_1$ (10 ng/ml) to a density-arrested, confluent monolayer of renal proximal tubule cells resulted in a phenotypic transformation of the monolayer to form solid aggregates of adherent cells as observed by light microscopy (magnification $\times 400$). Cells lining the surface of the cell aggregates possessed occasional broad based microvilli and tight junctional complexes, but no lumen formation was observed.

COMPARATIVE EXAMPLE 3

Simultaneous treatment of a confluent monolayer with TGF-$\beta_1$ (10 ng/ml) and EGF (1 nM) produced a similar morphologic transformation into cell aggregates which were, in general, larger than those seen with TGF-$\beta_1$, due to greater number of adherent cells within the condensed aggregate, as observed by light microscopy (magnification $\times 400$). However, no lumen formation or polarized epithelial phenotype was found.

COMPARATIVE EXAMPLE 4

The simultaneous exposure of the epithelial monolayer to TGF-$\beta_1$ (10 ng/ml) and RA (0.1 $\mu$M) promoted intracytoplasmic vacuolization as observed by light microscopy (magnification $\times 400$). However, these areas never developed into lumens with polarized epithelial phenotype, in contrast to the experiment with TGF-$\beta_1$, RA and EGF, administered in combination.

COMPARATIVE EXAMPLE 5

Treatment of the monolayer with RA alone (0.1 $\mu$m) or RA (0.1 $\mu$m) and EGF (1 nM) had no dramatic effect on the appearance of the monolayer.

These results indicate that transforming growth factor-$\beta_1$, epidermal growth factor, and all-trans retinoic acid play important roles in tubulogenesis.

Obviously, numerous modifications and variations of the present invention are possible in light of the above teachings. It is therefore to be understood that within the scope of the appended claims, the invention may be practiced otherwise than as specifically described herein.

What is claimed is:

1. An ex vivo renal tubule tissue system prepared by a process comprising culturing adult kidney cells in a culture medium comprising all-trans retinoic acid, transforming growth factor-$\beta_1$ and either epidermal growth factor or transforming growth factor-$\alpha$ in an amount effective for achieving tubulogenesis, wherein tubulogenesis is a phenotypic transformation of said cells such that condensed aggregates of tubule cells form about a central lumen wherein said lumen is bordered by cells possessing a polarized epithelial phenotype with extensive microvilli formation and tight junctional complexes along the lumenal border.

2. The renal tubule tissue system of claim 1, wherein said culture medium contains an insoluble factor selected from the group consisting of Type I collagen, Type IV collagen, laminin, proteoglycans, fibronectin, and combinations thereof.

3. The renal tubule tissue system of claim 1, wherein said culture medium comprises a soluble factor selected from the group consisting of fetal calf serum, prostaglandins, hydrocortisone, triodothyronine, selenium and combinations thereof.

4. The renal tubule tissue system of claim 1, wherein said culture medium comprises a soluble factor selected from the group consisting of fetal calf serum, prostaglandins, hydrocortisone, triodothyronine, selenium and combinations thereof, and an insoluble factor selected from the group consisting of Type I collagen, Type IV collagen, laminin, proteoglycans, fibronectin, and combinations thereof.

5. A method for growing kidney tubule stem cells ex vivo, comprising culturing adult kidney cells in the presence of all-trans retinoic acid, transforming growth factor-$\beta_1$, and either epidermal growth factor or transforming growth factor-$\alpha$, in an amount effective for achieving tubulogenesis, wherein tubulogenesis is a phenotypic transformation of said cells such that condensed aggregates of tubule cells form about a central lumen wherein said lumen is bordered by cells possessing a polarized epithelial phenotype with extensive microvilli formation and tight junctional complexes along the lumenal border.

6. The method of claim 5, wherein said culture medium contains an insoluble factor selected from the group consisting of Type I collagen, Type IV collagen, laminin, proteoglycans, fibronectin, and combinations thereof.

7. The method of claim 5, wherein said culture medium comprises a soluble factor selected from the group consisting of fetal calf serum, prostaglandins, hydrocortisone, triodothyronine, selenium and combinations thereof.

8. The method of claim 5, wherein said culture medium contains a soluble factor selected from the group consisting of fetal calf serum, prostaglandins, hydrocortisone, triodothyronine, selenium and combinations thereof, and an insoluble factor selected from the group consisting of Type I collagen, Type IV collagen, laminin, proteoglycans, fibronectin, and combinations thereof.

9. A method for effecting tubulogenesis in a renal cell culture ex vivo, comprising culturing adult kidney cells in the presence of all-trans retinoic acid, transforming growth factor-$\beta_1$, and either epidermal growth factor or transforming growth factor-$\alpha$ in an amount effective for achieving tubulogenesis, wherein tubulogenesis is a phenotypic transformation of said cells such that condensed aggregates of tubule cells form about a central lumen wherein said lumen is bordered by cells possessing a polarized epithelial phenotype with extensive microvilli formation and tight junctional complexes along the lumenal border.

10. The method of claim 9, wherein said culture medium contains an insoluble factor selected from the group consisting of Type I collagen, Type IV collagen, laminin, proteoglycans, fibronectin, and combinations thereof.

11. The method of claim 9, wherein said culture medium contains a soluble factor selected from the group consisting of fetal calf serum, prostaglandins, hydrocortisone, triodothyronine, selenium and combinations thereof.

12. The method of claim 9, wherein said culture medium contains a soluble factor selected from the group consisting of fetal calf serum, prostaglandins, hydrocortisone, triodothyronine, selenium and combinations thereof, and an insoluble factor selected from the group consisting of Type I collagen, Type IV collagen, laminin, proteoglycans, fibronectin, and combinations thereof.

13. A method for constructing and maintaining an ex vivo renal tubule tissue system, comprising culturing adult kidney cells in the presence of all-trans retinoic acid, transforming growth factor-$\beta_1$, and either epidermal growth factor or transforming growth factor-$\alpha$ in an amount effective for achieving tubulogenesis, wherein tubulogenesis is aa phenotypic transformation of said cells characterized by condensed aggregates of tubule cells forming about a central lumen wherein said lumen is bordered by cells possessing a polarized epithelial phenotype with extensive microvilli formation and tight junctional complexes along the lumenal border.

14. The method of claim 13, wherein said culture medium contains an insoluble factor selected from the group consisting of Type I collagen, Type IV collagen, laminin, proteoglycans, fibronectin, and combinations thereof.

15. The method of claim 13, wherein said culture medium contains a soluble factor selected from the group consisting of fetal calf serum, prostaglandins, hydrocortisone, triodothyronine, selenium and combinations thereof.

16. The method of claim 13, wherein said culture medium contains a soluble factor selected from the group consisting of fetal calf serum, prostaglandins, hydrocortisone, triodothyronine, selenium and combinations thereof, and an insoluble factor selected from the group consisting of Type I collagen, Type IV collagen, laminin, proteoglycans, fibronectin, and combinations thereof.

* * * * *

UNITED STATES PATENT AND TRADEMARK OFFICE
CERTIFICATE OF CORRECTION

PATENT NO. : 5,429,938

DATED : July 4, 1995

INVENTOR(S) : H. David HUMES

It is certified that error appears in the above-identified patent and that said Letters Patent is hereby corrected as shown below:

COLUMN 3, line 4, "TGF-βhd 1" should read --TGF-$\beta_1$--;

line 44, "trioodothyronine" should read --triiodothyronine--.

COLUMN 4, line 37, "laminal" should read --luminal--.

COLUMN 6, line 19, "celll" should read --cell--.

COLUMN 8, line 29, "triodothyronine" should read --triiodothyronine--;

line 34, "triodothyronine" should read --triiodothyronine--;

line 59, "triodothyronine" should read --triiodothyronine--;

UNITED STATES PATENT AND TRADEMARK OFFICE
CERTIFICATE OF CORRECTION

PATENT NO. : 5,429,938
DATED : July 4, 1995
INVENTOR(S) : J. David HUMES It is certified that error appears in the above-identified patent and that said Letters Patent is hereby corrected as shown below:

COLUMN 8, line 64, "triodothyronine" should read --triiodothyronine--.

COLUMN 9, line 22, "triodothyronine" should read --triiodothyronine--;

line 27, "triodothyronine" should read --triiodothyronine--.

COLUMN 10, line 7, "aa" should read --a--;

line 21, "triodothyronine" should read --triiodothyronine--;

line 26, "triodothyronine" should read --triiodothyronine--.

Signed and Sealed this

Second Day of July, 1996

Attest:

BRUCE LEHMAN

*Attesting Officer*  *Commissioner of Patents and Trademarks*